United States Patent
Shin et al.

(10) Patent No.: US 10,265,299 B2
(45) Date of Patent: Apr. 23, 2019

(54) COMPOSITION FOR PROMOTING HAIR GROWTH AND/OR HAIR RESTORATION CONTAINING PSORALIDIN

(71) Applicant: Amorepacific Corporation, Seoul (KR)

(72) Inventors: Seung Hyun Shin, Yongin-si (KR); Yong Deog Hong, Yongin-si (KR); Jun Seong Park, Yongin-si (KR); Yong Joo Na, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 15/561,591

(22) PCT Filed: Mar. 30, 2016

(86) PCT No.: PCT/KR2016/003228
§ 371 (c)(1),
(2) Date: Sep. 26, 2017

(87) PCT Pub. No.: WO2016/159642
PCT Pub. Date: Oct. 6, 2016

(65) Prior Publication Data
US 2018/0064683 A1    Mar. 8, 2018

(30) Foreign Application Priority Data

Mar. 31, 2015 (KR) .................. 10-2015-0045697

(51) Int. Cl.
| A61K 31/37 | (2006.01) |
| A61Q 7/00 | (2006.01) |
| A61K 8/49 | (2006.01) |
| A61K 9/00 | (2006.01) |
| A61Q 5/00 | (2006.01) |
| A61Q 5/02 | (2006.01) |
| A61Q 5/12 | (2006.01) |

(52) U.S. Cl.
CPC .............. *A61K 31/37* (2013.01); *A61K 8/498* (2013.01); *A61K 9/0014* (2013.01); *A61Q 5/00* (2013.01); *A61Q 5/02* (2013.01); *A61Q 5/12* (2013.01); *A61Q 7/00* (2013.01); *A61K 2800/92* (2013.01)

(58) Field of Classification Search
None
See application file for complete search history.

(56) References Cited

U.S. PATENT DOCUMENTS

2006/0269494 A1    11/2006    Gupta

FOREIGN PATENT DOCUMENTS

| JP | 06-321763 A | 11/1994 |
| JP | 2009-155235 A | 7/2009 |
| JP | 2012-046457 A | 3/2012 |
| JP | 10-2015-0019578 A | 2/2015 |
| KR | 10-0616342 B1 | 8/2006 |
| KR | 10-2014-0056990 A | 5/2014 |

OTHER PUBLICATIONS

Derwent Accession No. 2008-M3520 (evidencing Cai et al (CN 101213980 )) (Year: 2008).*
Mother Herbs & Agro Products (available online at http://www.motherherbs.com/psoralea-corylifolia.html as of Feb. 10, 2014, accessed Jul. 19, 2018) (Year: 2014).*
Internet Archive Report (containing Mother Herbs & Agro Products as of Feb. 10, 2014) (Year: 2014).*
Khushboo et al (Pharmacogn Rev 4:69-76, 2010) (Year: 2010).*
Ya Xiong, et al., "Identification of Wnt/β-catenin signaling pathway in dermal papilla cells of human scalp hair follicles: TCF4 regulates the proliferation and secretory activity of dermal papilla cell", The Journal of Dermatology, 2014, pp. 84-91, vol. 41, No. 1.
Tsutomu Soma, et al., "Hair-inducing ability of human dermal papilla cells cultured under Wnf/β-catenin signalling activation", Experimental Dermatology, 2012, pp. 307-309, vol. 21, No. 4.
Joanna Bronikowska, et al., "The Coumarin Psoralidin Enhances Anticancer Effect of Tumor Necrosis Factor-Related Apoptosis-Inducing Ligand (TRAIL)", Molecules, 2012, pp. 6449-6464, vol. 17, No. 6.
International Search Report for PCT/KR2016/003228 dated Jun. 15, 2016 [PCT/ISA/210].
Written Opinion for PCT/KR2016/003228 dated Jun. 15, 2016 [PCT/ISA/237].

* cited by examiner

*Primary Examiner* — Craig D Ricci
(74) *Attorney, Agent, or Firm* — Sughrue Mion, PLLC

(57) ABSTRACT

The present invention relates to a composition for promoting hair growth and hair restoration containing psoralidin or a derivative thereof, which can be widely used as an external skin preparation for promoting hair growth and hair restoration, a cosmetic composition or a pharmaceutical composition, as the composition has high stability for skin without side effects and is very effective in promoting hair growth or preventing hair loss by activating stem cells.

4 Claims, No Drawings

COMPOSITION FOR PROMOTING HAIR GROWTH AND/OR HAIR RESTORATION CONTAINING PSORALIDIN

CROSS REFERENCE TO RELATED APPLICATIONS

This application is a National Stage of International Application No. PCT/KR2016/003228 filed Mar. 30, 2016, claiming priority based on Korean Patent Application No. 10-2015-0045697 filed Mar. 31, 2015, the contents of all of which are incorporated herein by reference in their entirety.

TECHNICAL FIELD

The present invention relates to a composition for promoting hair growth and hair restoration containing psoralidin or a derivative thereof, which can be widely used as an external skin preparation for promoting hair growth and hair restoration, a cosmetic composition or a pharmaceutical composition, as the composition has high stability for skin without side effects and is very effective in promoting hair growth or preventing hair loss by activating stem cells.

BACKGROUND ART

Recently, due to an increase in social stress, along with environmental pollution, westernized dietary habits, such as instant food, frequent perming and dying of hair etc., the population of people with hair loss is gradually increasing. The cycle of hair growth can be divided into anagen stage during which the hair grows, catagen stage during which the hair growth ends and the hair bulb shrinks, telogen stage during which the dermal papilla stops its activity and the hair is retained in the scalp, and exogen stage during which the dermal papilla starts its activity or new hair grows, resulting in shedding of old hair.

The Anagen Stage (2 to 7 years) is the period during which the hair grows, and is divided into two stages of producing hair which grows outwards from the bulb into hair follicles and generating hard keratins in the hair follicles. The hair continues to grow itself until the catagen stage.

The Catagen Stage (2 to 3 weeks) is the period during which the growth ceases and the metabolism slows down while maintaining the shape of the hair, and keratin is not produced at this stage. The catagen stage accounts for 1% of total hair growth. At this stage, the hair bulb shrinks and divides into dermal papilla, and is surrounded by hair follicles and travels upwards, and the cell division is ceased.

The Telogen Stage (3 months) is the period during which the dermal papilla shrinks and the hair follicle gradually shrinks, and the hair root crawls upwards and falls out. It is the period of hair loss until the next stage of growth and lasts for 3 to 4 months.

Normal people have hair mostly in the anagen stage, but people with alopecia have hair mostly in the telogen stage, and thus a phenomenon of hair loss is visible with naked eye. As the hair loss progresses, the period of the anagen stage is shortened, resulting in the miniaturization of the hair. Accordingly, in order to treat the hair loss, it is important to allow the hair follicle in the telogen stage to enter rapidly to the anagen stage and to prolong the anagen stage.

Male-pattern alopecia is a phenomenon which occurs due to the male hormone testosterone, and when the testosterone is converted to dihydrotestosterone (DHT), which is a more stronger hormone, by 5α-reductase, this hormone acts on the hair follicle to induce the hair follicle from the anagen stage to the telogen stage, thereby causing hair loss. Accordingly, a method of inhibiting the production of DHT by 5α-reductase is mainly used to treat male-pattern alopecia.

Female-pattern alopecia is caused mainly by a decrease in the amount of estrogen after menopause. Minoxidil or estrogen are mainly used as therapeutic agents for female-pattern alopecia.

Alopecia areata is an autoimmune disease, but is caused by mental stress or genetic predisposition. The cause of the alopecia areata is fundamentally different, from those of androgenetic alopecia, and the treatment method is also different. Thus, methods of treating adrenocortical hormone are used, or methods of applying minoxidil to the affected area or of artificially inducing irritation to the affected area are used.

For such various and complex causes of hair loss, the components for promoting blood circulation, inhibiting male hormone function, strengthening the function of hair follicle, etc., are sold as commercialized products. However, none of them has shown a definite effect, and the problem of side effects is often raised. For example, it has been reported as adverse effects that minoxidil had sticky feeling of use and cause irritation to the skin. In the case of finasteride, it is currently used as a preparation for oral administration, but adverse effects, such as sexual dysfunction, have been reported according to its consumption, and it was inconvenient to use because it is expected to be effective only by oral administration.

PRIOR ART DOCUMENT

Patent Document

1. Korean Patent No. 10-0616342 (published on Aug. 29, 2006)

DISCLOSURE

Technical Problem

Substances that are conventionally used for promoting hair growth have many side effects and are inconvenient to use. Thus, in order to solve these problems, the present inventors have conducted intensive research to find a substance having high safety while having fewer side effects and having less constraints of usage, and found that psoralidin can provide such effects, thereby completing the present invention.

Accordingly, it is one object of the present invention to provide a composition exhibiting excellent hair growth and hair restoration effects by containing psoralidin or a derivative thereof.

Technical Solution

In order to achieve the object above, the present invention provides a composition for promoting hair growth and hair restoration containing psoralidin or a derivative thereof as an active ingredient.

Further, the present invention provides a use of psoralidin or a derivative thereof as a promoting agent for hair growth or restoration in the preparation of a cosmetic composition for hair growth or hair restoration.

Furthermore, the present invention provides a use of psoralidin or a derivative thereof as a promoting agent for hair growth or hair restoration in the preparation of a pharmaceutical composition for hair growth or hair restoration.

Advantageous Effects

The psoralidin used in the present invention is a natural compound present in plants and is used as medicinal herbs. Thus, it can be applied to the skin without side effects and can be very effective in promoting hair growth and preventing hair loss by activating stem cells.

DETAILED DESCRIPTION OF THE EMBODIMENTS

The present invention relates to a composition for promoting hair growth and hair restoration containing psoralidin or a derivative thereof as an active ingredient.

*Psoralea corylifolia* is a dried fruit of *Psoralea corylifolia* of leguminous plant, which is an annual plant, and is an often used medicinal herb for the treatment of osteoporosis and has been used to enhance sexual function by strengthening the Yang energy. The psoralidin used in the present invention is a natural phenolic compound found in the seeds of *Psoralea corylifolia*. When it is fed to animals, it is known to lower the levels of hormones of CRH (Corticotropin-releasing hormone) and corticosterone, which are stress hormones. (Reference Literature: "Antidepressant-like effects of psoralidin isolated from the seeds of *Psoralea Corylifolia* in the forced swimming test in mice". *Progress in neuro-psychopharmacology & biological psychiatry* 32 (2): 510-519). Further, it is known that psoralidin inhibits the phosphorylation of protein kinase Akt, thereby inhibiting the growth of androgen-independent prostate cancer cells both in vitro and in vivo (Reference Literature: "Total Synthesis of Psoralidin, an Anticancer Natural Product". *Journal of Organic Chemistry* 74 (7): 2750-2754).

The psoralidin used in the present invention has a structure represented by the following Chemical Formula 1.

[Chemical Formula 1]

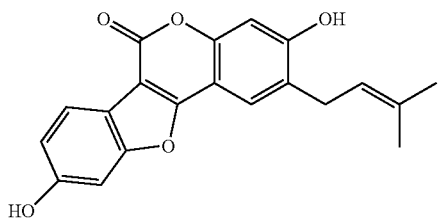 [SMILES: CC(C)=CCc1cc2c(cc1O)oc(=O)c1c3ccc(O)cc3oc21]

As used herein, the "derivative of psoralidin" refers to a chemically modified psoralidin, which means that a substituent has been modified using psoralidin produced either by isolation from nature or by synthesis.

The composition of the present invention may contain psoralidin or a derivative thereof in an amount of 0.01 to 10% by weight based on the total weight of the composition. When it is less than 0.01% by weight, a sufficient hair growth promoting effect cannot be achieved. When it exceeds 10% by weight, safety and formulation stability may be reduced.

The composition of the present invention activates stem cells by promoting the signal transfer of Wnt/beta-catenin by using psoralidin or a derivative thereof, which is an active ingredient, thereby being effective in promoting hair growth or preventing hair loss, and in addition, it prevents the progression to the catagen stage by controlling the hair follicle cycle and provides a hair growth promoting effect by allowing the hair to retain in the anagen stage for a long time.

Further, the composition of the present invention can provide an excellent hair restoration effect by promoting the proliferation of dermal papilla cells The composition for promoting hair growth and hair restoration according to the present invention, for example, can be formulated into a pharmaceutical composition, a cosmetic composition or an oral composition, which is an external skin preparation or heath food composition.

The pharmaceutical composition for promoting hair growth and hair restoration according to the present invention may further contain a pharmaceutical adjuvant such as a preservative, a stabilizer, a hydrating agent or an emulsifying accelerator, a salt and/or a buffer for controlling osmotic pressure, etc., and other therapeutically useful substances, and may be prepared into various formulations for oral or parenteral administration by a conventional method.

The formulation for oral administration may include, for example, tablet, pill, hard or soft capsule, liquid, suspension, emulsion, syrup, powder, dust, fine granule, granule, pellet, or the like. These formulations may include, in addition to the active ingredient, a surfactant, a diluent (e.g., lactose, dextrose, sucrose, mannitol, sorbitol, cellulose or glycine) or a lubricant (e.g., silica, talc, stearic acid and magnesium or calcium salt thereof or polyethylene glycol). The tablet may also include a binder such as magnesium aluminum, silicate, starch paste, gelatin, tragacanth, methyl cellulose, sodium carboxymethyl cellulose and polyvinylpyrrolidone, and may optionally include a pharmaceutical additive such as a disintegrant including starch, agar, alginic acid or a sodium, salt thereof, an absorbent, a colorant, a flavor, a sweetener, or the like. The tablet may be prepared according to a common mixing, granulation or coating method. Further, the formulation for parenteral administration may be a formulation for transdermal administration, and include, for example, injection, drop, ointment, lotion, gel, cream, spray, suspension, emulsion, suppository, patch, etc., but is not limited thereto.

The pharmaceutical composition according to the present invention can be administered parenterally, rectally, topically, transdermally, subcutaneously or the like. The pharmaceutical composition according to the present invention can be, for example, administered topically to the scalp.

Determination of the dose of the active ingredient is within the level of those skilled in the art, and the daily dose of a drug will vary depending on various factors, such as the progression of symptoms of a subject, time of onset, age, health condition, complications and the like. For adults, the composition can be typically administered at a dose of 1 μg/kg to 200 mg/kg, preferably, 50 μg/kg to 50 mg/kg once a day or three times a day, and the dose is not intended to limit the scope of the present invention in any way.

The composition for promoting hair growth and hair restoration according to the present invention may be a cosmetic composition. The external form of the cosmetic composition according to the above embodiment contains a cosmetically or dermatologically acceptable medium or base. It may be in any form suitable for topical application, for example, it may be provided in the form of solutions, gels, solids, paste anhydrous products, emulsions obtained by dispersing oil phase in aqueous phase, suspensions, microemulsions, microcapsules, microgranules, or ionic (liposomes) and non-ionic vesicle dispersants, or in the form of cream, skin toner, lotion, powder, ointment, spray or conceal stick, and these compositions may be prepared according to a conventional method in the art. In addition, the composition according to the present invention can be used in the form of foam or as an aerosol composition further containing a compressed propellant.

The composition for promoting hair growth and hair restoration according to the present invention may be formulated in the form of shampoo, hair treatment, scalp treatment, hair essence, hair pack, hair cream, hair tonic, general ointment and the like.

When the formulation of the present invention is paste, cream, or gel, the ingredients therein may include animal oil, vegetable oil, wax, paraffin, starch, tragacanth, cellulose derivatives, polyethylene glycol, silicone, bentonite, silica, talc, or zinc oxide, etc, as an ingredient for the carrier.

When the formulation of the present invention is powder or spray, the ingredients therein may include lactose, talc, silica, aluminum hydroxide, calcium silicate, or polyamide powder, as an ingredient for the carrier, and particularly, in the case of spray, it may further include a propellant, such as chlorofluorohydrocarbon, propane/butane or dimethyl ester.

When the formulation of the present invention is a solution or an emulsion, the ingredients therein include solvents, solubilizing agents, or emulsifying agents, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or sorbitan fatty acid ester, as an ingredient for the carrier.

When the formulation of the present invention is a suspension, the ingredients therein include liquid diluting agents, such as water, ethanol, or propylene glycol, suspending agents, such as ethoxylated isostearyl alcohol, polyoxyethylene sorbitol ester, and polyoxyethylene sorbitan ester, and microcrystalline cellulose, aluminum meta-hydroxide, bentonite, agar, or tragacanth, etc., as an ingredient for the carrier.

The composition of the present invention may further contain, in addition to the above-described components, functional additives and components contained in a general scalp or hair composition. The functional additives may include components selected from the group consisting of water-soluble vitamins, oil-soluble vitamins, polymer peptides, polysaccharides, sphingolipids and seaweeds extracts.

The cosmetic composition of the present invention may further be mixed with components contained in general cosmetic compositions, in addition to the above functional additives, if necessary. The components mixed and added to the functional additives may include oil and fat components, humectants, emollient agents, surfactants, organic or inorganic pigments, organic powder, UV absorbents, preservatives, sanitizers, antioxidants, vegetable extract s, pH adjusting agents, alcohols, coloring agents, flavoring agents, blood circulation promoters, cooling agents, adiaphoretics, purified water, or the like.

Further, the present invention relates to an external skin preparation including the composition for promoting hair growth and hair restoration, and the external skin preparation is a generic term that may include any substances applied to the skin exterior, and cosmetics and medicines of various formulations may be included therein.

Furthermore, the composition of the present invention may be in the form of a health food composition. In the health food composition of the present invention, the composition may be in the form of liquid or solid, and may be in the form, of tablets, capsules, soft capsules, pills, granules, beverages (drinks), diet, bars, chocolates, caramel or in confectionery formulations, but is not limited thereto. The health food composition of the present invention may contain excipients, saccharides, flavoring agents, coloring agents, oils and fats, proteins, and the like, as needed, in addition to the above effective ingredients.

In addition, the composition of the present invention may contain a skin absorption promoting substance to increase the hair growth and hair restoration promoting effects.

DETAILED DESCRIPTION OF THE EMBODIMENTS

Hereinafter, the composition and effects of the present invention will be described in more detail by way of Experimental Examples and Formulation Examples . However, these Experimental Examples and Formulation Examples are given for illustrative purposes only, and the scope of the invention is not intended to be limited by these Examples.

Reference Example 1

Preparation of Psoralidin

In order to test the efficacy of the composition of the present invention, psoralidin was purchased from BBP (Bio-BioPha Co., Yunnan Province, P. R. China; CAS No: 18642-23-4; BPP No: BPP02823) and used.

Experimental Example 1

Measurement of Hair Follicle Stem Cell Activity (WNT/β-catenin Luciferase Assay)

NIH3T3 (WNT) cells, which are hair follicle stem cells, were seeded in a 96 well plates (Nunc, Wiesbaden, Germany) at a density of 10000 cells/well and cultured for 24 hours (5% $CO_2$, 37° C.). Then, psoralidin was treated at varying concentrations (0, 0.01, 0.1, 1, 10 µM) for 24 hours. 100 µl of ONE-Glo reagent (Promega, Madison, Wis., USA) was added to each well of the 96-well plate and reacted for 3 minutes . After the reaction, the activity of stem eel ls was measured with a luminometer Victor (PerkinElmer, Waltham, Mass., USA).

As a result of the measurement, it was confirmed that the hair follicle stem cells were activated upon treatment with psoralidin, Experimental Example 2

Culture of Hair Follicle Organ and Observation of Hair Follicle Cycle

For the experiment, a hair transplant was performed to a 44-year-old man with a symptom of partial hair loss. Hair follicle samples of 4 groups each having 15 hair follicles were prepared with remaining follicle samples. William's E medium (Gibco, NY, USA) ) including 500 µl culture medium (2 mM L-glutamine (PAA, Coelbe, Germany), 10 µg/ml insulin, 10 ng/ml hydrocortisone (Sigma, St Louis, Mo.), 0.1% Fungizone (Gibco, NY, USA), 10 µg/ml streptomycin, and 100 U/ml penicillin (Gibco, NY, USA) was dispensed into a 24 well plate (Nunc, Wiesbaden, Germany). Then, the cells were cultured at a density of 5 to 6 cells per well on 500 ul of William's E medium (Gibco, NY, USA).

The cultured cell samples were treated with psoralidin at varying concentrations (0, 1, 10 µM). A sample not treated with psoralidin was used as a control and the medium was changed every 2 to 3 days. After the treatment with psoralidin, the hair follicle was photographed using a stereomicroscope (Dongwon CNS, Korea), and the life cycle of Image hair follicle was classified and schematized.

As a result of the measurement, the samples with psoralidin treatment remained longer in the anagen stage of the hair follicle cycle compared to the samples without psoralidin treatment, confirming that the speed of the progression to the catagen stage was significantly delayed.

This implies that psoralidin can be effective in promoting hair growth.

Formulation Example 1

Hair Tonic

A hair tonic was prepared in a conventional manner according to the composition shown in Table 1 below.

TABLE 1

| Ingredients | Weight ratio (%) |
| --- | --- |
| Ethanol | 50 |
| Menthol | 0.02 |
| Glycerin | 3 |
| Salicylic acid | 0.05 |
| Psoralidin | 0.5 |
| Flavoring and coloring agents | q.s. |
| Purified water | Balance (to 100) |

Formulation Example 2

Hair Lotion

A hair lotion was prepared in a conventional manner according to the composition shown in Table 2 below.

TABLE 2

| Ingredients | Weight ratio (%) |
| --- | --- |
| Cetostearyl alcohol | 2.0 |
| EDTA 2Na | 0.2 |
| Hydroxyethyl cellulose | 0.5 |
| Mineral oil | 5.0 |
| Psoralidin | 1.0 |
| Preservatives | q.s. |
| Flavoring and coloring agents | q.s. |
| Purified water | Balance (to 100) |

Formulation Example 3

Hair Nutritive Cosmetic Water

A hair nutritive cosmetic water was prepared in a conventional manner according to the composition shown in Table 3 below.

TABLE 3

| Ingredients | Weight ratio (%) |
| --- | --- |
| Wax | 4.0 |
| Polysorbate 60 | 1.5 |
| Sorbitan sesquioleate | 0.7 |

TABLE 3-continued

| Ingredients | Weight ratio (%) |
| --- | --- |
| Mineral oil | 10.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Psoralidin | 1.5 |
| Preservatives | q.s. |
| Flavoring and coloring agents | q.s. |
| Purified water | Balance (to 100) |

Formulation Example 4

Hair Shampoo

A hair shampoo was prepared in a conventional manner according to the composition shown in Table 4 below.

TABLE 4

| Ingredients | Weight ratio % |
| --- | --- |
| Purified water | Balance (to 100) |
| Psoralidin | 5.0 |
| Sodium lauryl sulfate | 36.0 |
| Cocamidopropyl betaine | 8.0 |
| Palmitidin maleate | 2.0 |
| Glycol Stearate | 1.5 |
| Polyquaternium 10 | 0.5 |
| Citric acid | 0.1 |
| Glycerin | 2.0 |
| Preservatives, flavoring and coloring agents | q.s. |

Formulation Example 5

Hair Conditioner

A hair conditioner was prepared in a conventional manner according to the composition shown in Table 5 below.

TABLE 5

| Ingredients | Weight ratio (%) |
| --- | --- |
| Purified water | Balance (to 100) |
| psoralidin | 1.0 |
| Propylene glycol | 2.0 |
| Cetyltrimethylammonium chloride | 1.0 |
| Cetyl alcohol | 3.0 |
| Stearyl alcohol | 3.0 |
| Mineral oil | 0.5 |
| Citric acid | 0.2 |
| Polydimethylsiloxane | 1.0 |
| Preservatives, flavoring and coloring agents | q.s. |

Formulation Example 6

Ointment

An ointment was prepared in a conventional manner according to the composition shown in Table 6 below.

TABLE 6

| Ingredients | Weight ratio (%) |
| --- | --- |
| Purified water | Balance (to 100) |
| Glycerin | 8.0 |
| Butylene glycol | 4.0 |
| Liquid paraffin | 15.0 |
| Beta glucan | 7.0 |
| Carbomer | 0.1 |
| Psoralidin | 5.0 |
| Caprylic capric triglyceride | 3.0 |
| Squalene | 1.0 |
| Cetearyl glucoside | 1.5 |
| Sorbitan stearate | 0.4 |
| Stearyl alcohol | 1.0 |
| Preservatives | q.s. |
| Flavoring agent | q.s. |

Formulation Example 7

Soft Capsule Formulation 50 mg of psoralidin, 80 to 400 mg of L-carnitine, 180 mg of soybean oil, 2 mg of palm oil, 8 mg of vegetable hydrogenated oil, 4 mg of yellow wax and 6 mg of lecithin are mixed and filled at 400 mg per capsule according to a conventional method to prepare a soft capsule.

Formulation Example 8

Tablet Formulation 50 mg of psoralidin, 200 mg of galactooligosaccharide, 60 mg of lactose and 140 mg of maltose are mixed and granulated using a fluidized bed drier, and then 6 mg of sugar ester was added and subjected to tableting to prepare a table formulation.

Formulation Example 9

Granule Formulation 50 mg of psoralidin, 250 mg of anhydrous crystalline glucose and 550 mg of starch are mixed and granulated to form granules using a fluidized bed granulator, and then filled into capsules.

Formulation Example 10

Drinking Formulation 50 mg of psoralidin, 10 g of glucose, 0.6 g of citric acid and 25 g of liquid oligosaccharide are mixed, and then 300 ml of purified water is added thereto, and the mixture is filled into a bottle. Then, the beverage is prepared by sterilizing at 130° C. for 4 to 5 seconds.

Although specific parts of the present invention have been described in detail, it will be apparent to those skilled in the art that these specific techniques are merely a preferred embodiment and that the scope of the present invention is not limited thereto. Therefore, the substantial scope or the present invention will be defined by the accompanying claims and their equivalents.

The invention claimed is:

1. A method for promoting hair growth or hair restoration, comprising applying an external skin preparation comprising psoralidin or a derivative thereof to an external part of a subject in need thereof, wherein the psoralidin or a derivative thereof is contained in an amount 0.01 to 10% by weight based on the total weight of the preparation.

2. The method as claimed in claim 1, wherein the external skin preparation is in a formulation of a cosmetic composition or a pharmaceutical composition.

3. The method as claimed in claim 1, wherein the preparation delays the regression of hair follicle cells.

4. The method as claimed in claim 1, wherein the preparation promotes the proliferation of dermal papilla cells.

* * * * *